United States Patent [19]

Gottlieb

[11] Patent Number: 4,710,380

[45] Date of Patent: Dec. 1, 1987

[54] TREATMENT OF AUTOIMMUNE DISORDERS WITH IMMUNOAMPLIFIERS

[75] Inventor: A. Arthur Gottlieb, New Orleans, La.

[73] Assignee: Imreg, Inc., New Orleans, La.

[21] Appl. No.: 848,210

[22] Filed: Apr. 4, 1986

[51] Int. Cl.⁴ .............................................. A61K 35/14
[52] U.S. Cl. ..................................... 424/101; 424/88; 514/19
[58] Field of Search ................... 424/101, 88; 514/19

[56] References Cited

U.S. PATENT DOCUMENTS 4,468,379 8/1984 Gottlieb ............................. 424/101
4,616,079 10/1986 Gottlieb ............................. 424/101

*Primary Examiner*—Sam Rosen
*Attorney, Agent, or Firm*—Richard H. Stern

[57] ABSTRACT

Therapeutic methods for treatment of rheumatoid arthritis, lupis, Type I diabetes, and other autoimmune disorders are described wherein amplifiers of the immune system response are administered to the subject. Instead of further increasing the hyperactive immune response, however, administering the amplifiers has the effect of reducing the excessive immune responsiveness. Compositions for such administration are also described.

18 Claims, No Drawings

TREATMENT OF AUTOIMMUNE DISORDERS WITH IMMUNOAMPLIFIERS

BACKGROUND

One important aspect of the human and animal immune system is the negative regulation of the immune responses that occur in response to the apparent presence of antigens. If no brake were placed on immune response, antibody-producing cells, for one example, would continue producing antibodies indefinitely. When the immune system is not appropriately regulated, several systemic malfunctions can occur. Defects of the operation of the immune system such as these have been associated with certain autoimmune disorders, in which the body reacts against its own tissue as if the tissue were a foreign body. Rheumatoid arthritis, multiple sclerosis, myasthenia gravis, lupus erthematosus, and insulin-dependent diabetes (type 1) are believed to be examples of such conditions.

The negative regulation of the immune system is believed to be controlled in part by cells known as "suppressor cells." Human suppressor cells include T8 cells (which are also known as T8+ or Leu+2 cells); there may be other human suppressor cells. Suppressor cells act in concert with other cells to bring about a normal immune response, what may be considered immune system homeostasis. Autoimmune defects of the type described above may result from insufficient production, potentiation, or operation (which are collectively referred to at times hereinafter as "activation") of suppressor cells.

Copending patent applications of the inventor describe methods for assaying amplifier immune reserve (Gottlieb, "Diagnostic Methods for Immune Function," Ser. No. 830,728) and suppressor reserve (Gottlieb, "Determination of Suppressor Functional Reserve," Ser. No. 832,016), functions of the human and animal immune system to which the present invention relates; the latter is particularly pertinent. An abstract published in March 1985 (Sizemore, Farmer, and Gottlieb, "Enhancement of nonspecific suppressor T cell activity by immunomodulators derived from human leukocyte dialysates," Fed. Proceedings 947, No. 3133) refers in general terms to various aspects of the procedures described herein.

Other useful background on amplifiers and suppressors is found in Gottlieb U.S. Pat. No. 4,468,379, in copending Gottlieb patent application Ser. No. 643,724, and in copending Gottlieb patent application Ser. No. 813,586. These and the preceding patent applications in various respects distinguish immunomodulators, of which amplifiers and suppressors are each subsets, from the "transfer factor" of prior art. Transfer factor, for example, has a specific effect with regard to a particular antigen, for which it is said to transfer immune response from donor to donee although the latter may never have been previously exposed to the antigen in question. Immunomodulators, however, are nonspecific and their administration generally affects immune response only with respect to antigens to which the donee has previously (or at least concurrently) been exposed.

It has been observed that rheumatoid arthritis patients may display decreased production of interleukin-2 (IL-2) and decreased natural killer (NK) cell activity. See Combe, Pope, Darnell, Kincaid, and Talal, 133 J. Immunol. 709 (1984); Combe, Pope, Fishbach, Dranell, Baron, and Talal, 59 Clin. Exp. Immunol. 520 (1985). These observations tend further to confirm the hypothesis that the disease has a significant immune system component, since production of IL-2 and NK cell activity are considered to reflect the state of the subject's immune system function.

SUMMARY OF THE PRESENT INVENTION

This invention relates to the treatment of autoimmune disorders, particularly rheumatoid arthritis, with immunoamplifiers. The inventor has discovered that it is possible to alleviate adverse symptoms of autoimmune, hyperactive cell-mediated immune system response by the administration of an effective dosage amount of an amplifier of the immune system. Rather than further amplifying the patient's immune response and thus worsening the severity of his or her autoimmune symptoms, as might be anticipated, appropriate dosage with amplifier alleviates the symptoms.

The inventor hypothesizes that the amplifier acts to correct an imbalance of the immune system in these patients, which causes the suppressor system of the patient not to be fully operative. The amplifier appears to activate a suppressor-inducer subset of T4 cells, and possibly acts directly on T8 suppressor cells as well or in addition.

The inventor has observed that, in an individual with a normal immune system, a very small dosage of amplifier produces a small amplifier effect (increase in immune response), and a larger dosage produces a larger effect. This effect continues until a point is reached at which further increases in the amount of amplifier administered to the subject do not produce an increase in amplifier effect, but instead produce a decrease. The dosage zone prior to this point may therefore be termed the "non-paradoxical dosage range," and the dosage zone beginning at this point may therefore be termed the "paradoxical dosage range," since after this point increases in dosage produce decreases in amplifier effect. The inventor hypothesizes that the administration of amplifier, in the non-paradoxical dosage range, may correct the imbalance.

DETAILED DESCRIPTION OF PREFERRED EMBODIMENT

A group of active rheumatoid arthritis patients was selected. Each patient had on average at least 14 joints actively affected. The patients were each tested for immune response to the administration of the known mitogen phytohemoagglutin (PHA) (Wellcome Reagents HA 16), and each displayed a below normal proliferative response to the administration of PHA.

Each patient was given a subcutaneous injection of Amplifer Beta of Example 7 of the copending Gottlieb patent application, "Immunoamplifiers and processes for extraction thereof," Ser. No. 643,724 (the '724 application), equivalent to the amount derived from 400,000 leukocytes. The dose was repeated two weeks later and then another two weeks later. The patients were followed for another month. No side effects attributable to the use of Amplifier Beta were reported. (The inventor has observed that the appropriate biweekly dosage of Amplifier Beta for increasing a hypoimmune system response is approximately the amount derived from 400,000 leykocytes.)

The appropriate biweekly dosage was determined by trial and error. However, several things may be noted about the appropriate dosage amount here. First, it is at least as great as that which the inventor has found appropriate for treating hypoimmune conditions, such as AIDS and AIDS-Related Complex (ARC). Prior work of the inventor has established a rule of thumb for treating such hypoimmune conditions, which is that the appropriate therapeutic dosage is approximately $10^5$ to $10_6$ times the dosage that produces maximal dermal response in a test of delayed hypersensitivity skin reaction to antigen (DH skin test), for 0.05 ml of tetanus toxoid (½ dilution of standard fluid tetanus toxoid, Squibb/Connaught). Second, it is usually less than 100 times the hypoimmune therapeutic dosage. This places the appropriate dosage here in the range of approximately $10^5$ to $10^8$ times the amount of amplifier administered in a skin test to secure maximal DH response against 0.05 ml tetanus toxoid (as above). In the inventor's opinion, the center of that $10^5$ to $10^8$ range ($3 \times 10^6$, logarithmically) is approximately optimal. If it is desired to give weekly dosages, the optimal amount is probably somewhat less than half the optimal biweekly dosage amount. Similarly, the optimal monthly dosage is probably somewhat more than twice (or more than twice 30/14) the optimal biweekly dosage, due in both cases to nonlinear effects.

Various indices of immune response were monitored: delayed hypersensitivity skin reaction to antigen, peripheral blood proliferative response to PHA and pokeweed mitogen, and NK cell activity. Typically, the administration of Amplifier Beta resulted in responses similar to those described in the '724 application and in Gottlieb U.S. Pat. No. 4,468,379.

There was clear evidence of temporary improvement in joint pain, as reported by the patients. After treatment with Amplifier Beta was discontinued, the patients reported worsening of their symptoms, and in particular an increase in joint pain over the level of pain experienced during treatment.

Examples 1-4, below, are constructed from the data gathered in the foregoing tests and represent average data.

EXAMPLE 1

SCREENING AND PHA TEST

Patient A has 14 joints actively affected by rheumatoid arthritis. A's proliferative response to administration of 125 nanograms (ng)/ml of PHA (Wellcome Reagents HA 16) is measured by the standard methods well known to those experienced in the art. The result is 21,021 counts per minute (CPM), which is substantially below a noraml response, which, typically, would be 33,384 CPM. (The time is designated as Week 0.)

EXAMPLE 2

ADMINISTRATION OF BETA

Immediately after the PHA test of Example 1, Patient A is given a subcutaneous injection of 0.1 ml of solution containing Amplifier Beta in sterile saline. The quantity of Amplifier Beta is equivalent to that derived from 400 thousand leukocytes. (The time is still designated Week 0.)

The injection is repeated in two weeks (Week 2), and then again in another two weeks (week 4).

EXAMPLE 3

FURTHER PHA TESTS

The PHA test of Example 1 is repeated every week for eight weeks (Weeks 1-8), using not only the 125 ng/ml dosage of Example 1 but also 250, 500, and 1000 ng/ml except that data is lacking for Week 7. The results are tabulated below:

| Week | Response (CPM) | | | |
|---|---|---|---|---|
| | 125 ng/ml | 250 ng/ml | 500 ng/ml | 1000 ng/ml |
| 0 | 21012 | 57201 | 116054 | 137292 |
| 1 | 16338 | 45221 | 81442 | 103535 |
| 2 | 22579 | 35561 | 56817 | 76951 |
| 3 | 26163 | 34650 | 58790 | 82466 |
| 4 | 27565 | 56330 | 100588 | 128055 |
| 5 | 35957 | 84560 | 154923 | 182822 |
| 6 | 37579 | 82833 | 121322 | 144480 |
| 8 | 55087 | 121437 | 217471 | 237286 |

Tests of other immune system indices are consistent with the foregoing results.

EXAMPLE 4

CLINICAL RESULTS

Patient A reports decreased joint pain during Weeks 2-4, and increased joint pain after Week 5.

The therapy for rheumatoid arthritis may be extended to other autoimmune conditions, such as those described in the first paragraph of this specification. If desired, the dosage of amplifier may be titrated to the patient's condition by the method described in Examples 9 and 11 of the '724 application.

EXAMPLE 5

TREATMENT OF DIABETES

Patient B suffers from insulin-dependent diabetes (type 1). The patient's lymphocytes display diminished capacity to produce IL-2.

Patient B is given the treatment described in Example 2, for 12 weeks.

IL-2 production is screened and is found to rise to within 20% of normal and remain at approximately that level throughout the test period.

After Week 2, the symptoms described in the first paragraph subside. After Week 14, the symptoms begin to return.

The therapy may be used with other amplifiers than Amplifier Beta. Amplifier Zeta-2 of the '724 application may be so used, and so too may the tripeptide TGG and its derivatives, described in the copending Gottlieb patent application, "Tripeptides affecting immune response," Ser. No. 813,586.

EXAMPLE 6

USE OF ZETA-2

The procedure of Examples 1-4 is repeated, substituting Amplifier Zeta-2 for Amplifier Beta. The results are the same.

The therapy described here may be extrapolated to mammalian veterinary use by known methods, taking due account of the differences in body weight of the subjects. In this connection, the use of TGG and its derivates is preferred to Amplifiers Beta or Zeta-2.

GENERAL CONCLUDING REMARKS

The above described procedures disclose what the inventor believes is a unique and hitherto unknown method of treating human or animal subjects for the symptoms of autoimmune disorders. While the invention has been described primarily in connection with a specific and preferred embodiment thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made.

As used in the claims, the term "the amount of said amplifier found to produce a maximal delayed type hypersensitivity response to antigen in a skin test" refers to the rul of thumb procedure discussed before Example 1. That is, the amount of said amplifier found to produce a maximal DH response to antigen in a skin test is established by making a series of DH skin tests with various dilutions of amplifier, against a suitable antigen to which the test subject is sensitive, such as tetanus toxoid (in the amount stated), or by using an equivalent kind of DH test to determine where the parodoxical range starts for DH reaction. While the inventor has found it most expedient to provide biweekly dosages, that is a matter of convenience and one for medical choice. In claims such as claim 17, wherein a biweekly dosage is specified, it would be within the scope of the invention to multiply or divide the dosage, as suggested preceding Example 1, in order to provide less or more frequent administration of the dosage. Moreover, there appears to be nothing to prevent the use of a larger dosage, such as one well into the paradoxical dosage range. However, to do so would require more active ingredient and thus increase the cost of providing the medication, without apparent increase in benefit. (The inventor also considers it poor medical practice to administer any more of a drug than is needed to accomplish the therapeutic purpose, since the result may be to cause some other undesired effect.) Hence, it is considered that it would be within the scope of the invention and its teachings to use unnecessarily large dosages, when that is not done for a substantial reason other than to avoid the claims. Thus, for the purposes of claim 3, "an effective dosage amount" is considered to include an amount in excess of what the specification teaches is effective, which is to say "at lest an effective dosage amount."

I claim:

1. A method of treating human or mammalian subjects for disorders characterized by hyperactive immune response, comprising the administration to said subject of an effective dosage amount of an amplifier of the immune system in a pharmaceutically acceptable carrier.

2. The method of claim 1 wherein said disorder is an autoimmune disorder.

3. The method of claim 1 wherein said subject is human.

4. The method of claim 3 wherein said disorder is rheumatoid arthritis.

5. The method of claim 3 wherein said disorder is lupus.

6. The method of claim 3 wherein said disorder is multiple sclerosis.

7. The method of claim 3 where said disorder is myasthenia gravis.

8. The method of claim 3 where said disorder is diabetes mellitus (type 1).

9. The method of claim 3 wherein said dosage amount is titrated by assaying the subject's immune response.

10. The method of claim 3 wherein said dosage amount is one in the nonparadoxical dosage range.

11. The method of claim 3 wherein said dosage amount is approximately $10^5$ to $10^8$ times the amount of said amplifier found to produce a maximal delayed type hypersensitivity response to antigen in a skin test, and said administration is approximately biweekly.

12. The method of claim 11 wherein said dosage amount is approximately $3 \times 10^6$ times the amount of said amplifier found to produce a maximal delayed type hypersensitivity response to antigen in a skin test, and said administration is approximatley biweekly.

13. The method of claim 1 wherein said amplifier is TGG.

14. The method of claim 3 wherein said amplifier is Amplifier Beta.

15. The method of claim 3 wherein said amplifier is Amplifier Zeta-2.

16. As an article of manufacture, an effective biweekly dosage amount of an amplifier of the immune system for the treatment of an autoimmune disorder, said dosage amount being in a pharmaceutically acceptable carrier, and said dosage amount being approximately $10^5$ to $10^8$ times the amount of said amplifier found to produce a maximal delayed type hypersensitivity response to antigen in a skin test.

17. The article of manufacture of claim 16 wherein said dosage amount is approximately $3 \times 10^6$ times the amount of said amplifier found to produce a maximal delayed type hypersensitivity response to antigen in a skin test.

18. A method of treating a patient for rheumatoid arthritis comprising administering to said patient, biweekly, the quantity of Amplifier Beta derived from approximately 400,000 leukocytes.

* * * * *